US010323272B1

(12) United States Patent
Rabbani et al.

(10) Patent No.: US 10,323,272 B1
(45) Date of Patent: Jun. 18, 2019

(54) NUCLEIC ACID PROBES FOR IN SITU HYBRIDIZATION

(71) Applicant: Enzo Biochem, Inc., New York, NY (US)

(72) Inventors: Elazar Rabbani, New York, NY (US); Jack Coleman, East Northport, NY (US); Maurizio Mauro, Long Island City, NY (US)

(73) Assignee: Enzo Biochem, Inc., New York, NY (US)

( * ) Notice: Subject to any disclaimer, the term of this patent is extended or adjusted under 35 U.S.C. 154(b) by 0 days.

(21) Appl. No.: 16/053,138

(22) Filed: Aug. 2, 2018

Related U.S. Application Data

(60) Provisional application No. 62/624,249, filed on Jan. 31, 2018.

(51) Int. Cl.
*C12P 19/34* (2006.01)
*C12Q 1/6841* (2018.01)

(52) U.S. Cl.
CPC ............ *C12Q 1/6841* (2013.01); *C12P 19/34* (2013.01)

(58) Field of Classification Search
None
See application file for complete search history.

(56) References Cited

U.S. PATENT DOCUMENTS

| 6,420,539 | B1 | 7/2002 | Kramer et al. | |
|---|---|---|---|---|
| 8,512,953 | B2 | 8/2013 | Saito et al. | |
| 2016/0068903 | A1* | 3/2016 | Zhou | C12Q 1/686 536/24.33 |

OTHER PUBLICATIONS

Lehninger, Biochemistry, 1970, Worth Publishers, Inc. New York, pp. 241-251.*
Anderson et al., "Incorporation of reporter-labeled nucleotides by DNA polymerases," *BioTechniques*, vol. 38, No. 2, pp. 257-263 (2005).
Antson, Dan-Oscar, "Genotyping RNA and DNA Using Padlock Probes," *Acta Universitatis Upsaliensis*, Comprehensive Summaries of Uppsala Dissertations from the Faculty of Medicine 1050, 40 pages (2001).
Marimuthu et al., "Single-stranded DNA (ssDNA) production in DNA aptamer generation," *The Royal Society of Chemistry*, vol. 137, pp. 1307-1325 (2012).
Melton et al., "Efficient in vitro synthesis of biologically active RNA and RNA hybridization probes from plasmids containing in bacteriophage SP6 promoter," *Nucleic Acids Research*, vol. 12, No. 18, pp. 7035-7056 (1984).
Thorstenson et al., "An Automated Hydrodynamic Process for Controlled, Unbiased DNA Shearing," *Genome Methods*, vol. 8, pp. 848-855 (1998).

* cited by examiner

*Primary Examiner* — James Martinell
(74) *Attorney, Agent, or Firm* — Paul Diamond, Esq.

(57) ABSTRACT

The invention provides nucleic acid hybridization probes having improved detectability that include a plurality of first segments consecutively complementary to a target nucleic acid sequence and, between neighboring first segments, a nucleic acid spacer segment which is not complementary to the target nucleic acid sequence and which may include labeled nucleic acid residues. Also provided by the invention are methods for making the probes, methods for using the probes, and compositions of matter that include the probes hybridized to target nucleic acid molecules.

10 Claims, 3 Drawing Sheets

Specification includes a Sequence Listing.

PRIOR ART

NUCLEIC ACID PROBES FOR IN SITU HYBRIDIZATION

CROSS-REFERENCE TO RELATED APPLICATIONS

This application claims the benefit of U.S. provisional application Ser. No. 62/624,249 filed Jan. 31, 2018, which is hereby incorporated by reference in its entirety.

FIELD OF THE INVENTION

The present invention relates to the field of nucleic acid hybridization probes.

SEQUENCE LISTING

The instant application contains a Sequence Listing which has been submitted electronically in ASCII format and is hereby incorporated by reference in its entirety. Said ASCII copy, created on Aug. 1, 2018, is named ENZ-117-SL_ST25.txt and is 3,555 bytes in size.

BACKGROUND OF THE INVENTION

In situ hybridization (ISH) involves the hybridization of a labeled complementary DNA, RNA or modified nucleic acid strand, i.e., a nucleic acid probe, to a specific DNA or RNA sequence that may be present in a tissue or cell specimen and the detection of the hybridized probe. Probes are commonly labeled with haptens for affinity-based, enzyme-mediated colorimetric detection, or fluorescent moieties for direct fluorescent detection (so-called fluorescence in situ hybridization; "FISH"), or radioactively labeled. Human papillomavirus (HPV) infection is a well-established risk factor for the development of cervical carcinomas and precancerous lesions and, in recent years, the use of in situ hybridization for the detection of HPV genes or transcripts in human cervical cell specimens has been adopted.

What is needed and provided by the present invention are improved nucleic acid hybridization probes for in situ hybridization applications.

SUMMARY OF THE INVENTION

One embodiment of the invention provides a non-naturally occurring linear nucleic acid molecule having a 5' end and a 3' end, which includes:
  a series of first nucleic acid segments consecutively complementary to a preselected nucleic acid target sequence; and
  between each adjacent pair of first nucleic acid segments, a spacer nucleic acid segment,
    wherein the spacer segments are not substantially complementary to the preselected nucleic acid target sequence, and
    wherein at least some nucleic acid monomers of the spacer segments are labeled with detectable labels, such as fluorescent moieties or haptens.
The spacer segments may be at least substantially not complementary to the first segments. The linear nucleic acid molecule may further include at one or both of the 5' end and the 3' end an additional spacer nucleic acid segment.

Another embodiment of the invention provides a non-naturally occurring linear nucleic acid molecule having a 5' end and a 3' end, which includes:
  a series of first nucleic acid segments consecutively complementary to a preselected nucleic acid target sequence; and
  between each adjacent pair of first nucleic acid segments, a spacer nucleic acid segment,
    wherein the spacer segments are not substantially complementary to the preselected nucleic acid target sequence, and
    wherein at least some nucleic acid monomers of the spacer segments are labeled with an allyl amine group, for example, at least some of the monomers may be aminoallyl ribonucleotides or aminoallyl deoxyribonucleotides.
The spacer segments may be at least substantially not complementary to the first segments. The linear nucleic acid molecule may further include at one or both of the 5' end and the 3' end an additional spacer nucleic acid segment.

A further embodiment of the invention provides an in vitro hybrid composition of matter that includes:
  (i) any of the non-naturally occurring nucleic acid molecules (or probe embodiments) described herein; and
  (ii) a naturally occurring (biological) nucleic acid target molecule including the nucleic acid target sequence,
wherein (i) is hybridized to (ii) by way of the first nucleic acid segments.

A still further embodiment of the invention provides a method for detecting a target nucleic acid sequence in a sample that includes the steps of:
  providing a non-naturally occurring nucleic acid molecule (or any of the probe embodiments) as described herein;
  contacting the non-naturally occurring nucleic acid molecule (or probe embodiment) with an isolated biological sample that may contain nucleic acid molecules that include the preselected nucleic acid target sequence under conditions permitting hybridization of the non-naturally occurring nucleic acid molecule (or probe embodiment) to the nucleic acid molecules including the preselected nucleic acid target sequence if present in the sample; and
  detecting label of any of the non-naturally occurring nucleic acid molecule (or probe embodiment) that may be hybridized to the nucleic acid molecules that include the preselected nucleic acid target sequence if present in the sample.
The method may further include a washing step after the contacting step and before the detecting step to remove non-naturally occurring linear nucleic acid molecule/probe that is not specifically hybridized to a target nucleic acid molecule in the sample/specimen. The detecting step may include a 2D or 3D visualization/image capture using microscopy as known in the art.

Another embodiment of the invention provides a method for preparing a nucleic acid hybridization probe composition for a nucleic acid target of interest that includes the steps of:
  providing an in vitro mixture of
    (a) a nucleic acid template molecule, wherein the template sequence encodes a non-naturally occurring linear nucleic acid molecule having a 5' end and a 3' end and including
      a series of first nucleic acid segments consecutively complementary to a preselected nucleic acid target sequence, and
      between each adjacent pair of first nucleic acid segments, a spacer nucleic acid segment,
        wherein the spacer segments are not substantially complementary to the preselected nucleic acid target sequence;

(b) a template-directed nucleic acid polymerase capable of synthesizing a nucleic acid molecule including labeled nucleic acid monomers and complementary to at least part of the template using the template molecule, and
(c) a mixture of different nucleic acid monomers such as ribonucleotides or deoxy ribonucleotides (required by the polymerase synthesize a complementary strand using the template) wherein at least some of said nucleic acid monomers may be labeled (chemically and/or radioactively); and incubating said mixture under conditions permissive for template-directed nucleic acid synthesis by the polymerase, wherein said nucleic acid molecule including labeled nucleic acid monomers (residues) if present in mixture (c) and complementary to at least part of the template using the template molecule is thereby synthesized in quantity.

The spacer segments may be at least substantially not complementary to the first segments. The linear nucleic acid molecule may further include at one or both of the 5' end and the 3' end an additional spacer nucleic acid segment. In a variation, the mixture of different nucleic acid monomers includes at least some nucleic acid monomers that are labeled.

A further embodiment of the invention provides a method for preparing a nucleic acid hybridization probe composition for a nucleic acid target of interest that includes the steps of:
providing an in vitro mixture of
(a) a DNA construct including an RNA promoter operably linked to a template DNA sequence, wherein the template sequence encodes a non-naturally occurring linear nucleic acid molecule having a 5' end and a 3' end and including
a series of first nucleic acid segments consecutively complementary to a preselected nucleic acid target sequence; and
between each adjacent pair of first nucleic acid segments, a spacer nucleic acid segment,
wherein the spacer segments are not substantially complementary to the preselected nucleic acid target sequence,
(b) a mixture of different ribonucleotide monomers wherein at least some of said ribonucleotide monomers may be labeled (chemically and/or radioactively);
(c) an RNA polymerase capable of transcribing an RNA molecule including the labeled ribonucleotides from the template under control of the promoter; and incubating said mixture under conditions permissive for transcription of the RNA molecule by the RNA polymerase, wherein said RNA molecule is thereby transcribed in quantity.

The spacer segments may be at least substantially not complementary to the first segments. The linear nucleic acid molecule may further include at one or both of the 5' end and the 3' end an additional spacer nucleic acid segment. In a variation, the mixture of different ribonucleotide monomers includes at least some ribonucleotide monomers that are labeled and which are incorporated into the transcribed RNA.

Still another embodiment of the invention provides a method for preparing a nucleic acid hybridization probe composition that includes the steps of:
providing a quantity of a non-naturally occurring linear nucleic acid molecule, such as an RNA molecule or a DNA molecule, having a 5' end and a 3' end, that includes:
a series of first nucleic acid segments consecutively complementary to a preselected nucleic acid target sequence; and
between each adjacent pair of first nucleic acid segments (and optionally at one or both of the 5' end and the 3' end), a spacer nucleic acid segment,
wherein the spacer segments are not substantially complementary to the preselected nucleic acid target sequence,
wherein the spacer segments are not substantially complementary to the first segments,
wherein the spacer segments are not substantially complementary to each other, and
wherein the spacer segments may include nucleic acid monomers having a chemical label, such as but not limited to an allyl amine group or a detectable label such as a hapten label or a fluorescent label, or the nucleic acid monomers of the spacer segments, or the non-naturally occurring linear nucleic acid molecule in its entirety, may not comprise a chemical label; and
fragmenting the quantity of a non-naturally occurring linear nucleic acid molecule to obtain a fragmented nucleic acid hybridization probe composition.

The non-naturally occurring linear nucleic acid molecule may, for example, be at least 500 monomers in length, such as 500-2500 monomers in length, or any subrange therein, and the fragmenting step may, for example, result in a composition including fragments 100-500 monomers in length, or any subranges therein such as 200-500 monomers in length, such as 200-400 monomers in length, such as 250-350 monomers in length. The length of the first segments and the spacer segments may be selected so that at least some fragments, such as those in the aforementioned length ranges, maintain a structure having adjacent first segments connected by an intervening spacer segment. For example, first segments may be 40-60 monomers in length, or any subrange or value therein, and spacer segments may be around 20-30 monomers in length or any subrange or value therein.

In any of the embodiments of the invention and variations thereof described herein, the series of first nucleic acid segments may, for example, include at least 2, at least 3, at least 4, or at least 5 first nucleic acid segments. In any of the embodiments of the invention and variations thereof described herein, the series of first nucleic acid segments may, for example, include in the range of 2-30 first nucleic acid segments or any subrange or whole number of first nucleic acid segments therein. In any of the embodiments of the invention and variations thereof described herein, the series of first nucleic acid segments may, for example, include in the range of 3-30 first nucleic acid segments or any subrange or whole number of first nucleic acid segments therein.

Additional features, advantages, and embodiments of the invention may be set forth or apparent from consideration of the following detailed description, drawings if any, and claims. Moreover, it is to be understood that both the foregoing summary of the invention and the following detailed description are exemplary and intended to provide further explanation without limiting the scope of the invention as claimed.

DETAILED DESCRIPTION OF THE INVENTION

In one aspect, the invention provides nucleic acid hybridization probes having improved detectability. In one embodiment, the probes include a plurality of first segments sequentially complementary to a target nucleic acid sequence and, between neighboring first segments, a nucleic acid spacer segment which is not complementary to the target nucleic acid sequence and not complementary to the first segments, and which includes labeled nucleic acid residues. A spacer segment may optionally also be disposed at either or both of the termini. The labeled nucleic acid monomers of the spacer segments may include labels such as biotin and/or digoxigenin, for secondary detection, e.g., by immunohistochemistry, and/or fluorescently labeled nucleic acid monomers. Detectability is improved for the following reasons. First, the ability to select the sequence of the spacer segments permits these segments to be densely labeled while not affecting the sequence specificity of the complementary first segments. And, second, with particular relevance to indirect detection methods such as immunohistochemistry, when the probe is hybridized to the target sequence, the labeled spacer segments loop out, thereby providing less-hindered access to the labeled monomers of the segment by secondary detection reagents such as avidin and streptavidin (biotin binders) and enzyme conjugates thereof, or anti-digoxigenin antibodies and enzyme conjugates thereof. Such enzyme conjugates may, for example, include those well-recognized in the art such as horseradish peroxidase conjugates and alkaline phosphatase conjugates.

The sequences of at least some of the spacer segments, such as at least half of the spacer segments or all of the spacer segments, may be at least substantially the same, for example, at least 90% or at least 95% or at least 98% identical, or exactly identical to each other. The sequence(s) of the spacer segments may be at least substantially not self complementary.

By consecutive or sequential arrangement of the first segments of a nucleic acid molecule/probe embodiment of the invention what is meant is, in the order the first segments occur in the probe in the 5' to 3' direction, these segments hybridize in the same order along the target sequence in its 3' to 5' direction. There may be sequence gaps ("gaps") or no-gaps between the 3' end of a given first segment of a probe and the '5 end of the next adjacent first segment of the probe (proceeding in the 3' direction of the probe). The gaps correspond to sequence elements that would be present in a full complementary strand to the target nucleic acid that are not provided by or present between the first nucleic acid segments when they are hybridized to the target. Gaps, if present, may, for example, be in the range of 1-30 residues/nt long with respect to the target strand, or any subrange or numerical value therein such as but not limited to 4-12 residues long. In one variation, a nucleic acid molecule/probe embodiment of the invention has a sequence such that there is a gap between each neighboring first segment when hybridized to the target strand.

The probes of the invention may, for example, be composed of RNA and/or DNA and/or labeled analogs thereof, in any combination thereof. The probes of the invention may be synthesized synthetically, for example, using conventional phosphoramidite chemistry and reagents therefor. The probes of the invention may also be synthesized enzymatically, for example, by template-directed nucleic acid synthesis such but not limited to RNA transcription using common viral promoter systems (e.g., T7 and SP6) for synthesizing RNA probes, and polymerase chain reaction (PCR) for synthesizing DNA probes. For such enzymatic syntheses, labeled nucleotides or ribonucleotides may be included in the reaction mixture for incorporation into the product. For template directed synthesis, it should be understood that the monomer mix will include all complementary monomers to synthesize the complementary strand of the template and may generally include nucleic acid monomers having all four bases (A, G, T/U, C).

In one embodiment, one or more or all of the spacer segments include labeled nucleic acid monomers (labeled residues). Each or all of the target-complementary first segments may include or exclude labeled nucleic acid monomer(s). Where one or more or all of the target-complementary first segments includes labeled nucleic acid monomer(s), the labeled monomers may be the same and/or different than the labeled monomers of the spacer segments. When the probes are chemically synthesized, the type and position of labeled monomers in the probe can be predetermined and precisely controlled, for example, providing labeling only in the spacer segments. When synthesis is polymerase-mediated (template-directed), assuming the same types of bases occur in both the target-complementary first segments and the spacer segments, both will be labeled by incorporation of the labeled nucleic acid monomers.

In related embodiments, the probe may be labeled as above or have the same structure but be unlabeled, and (for either case) secondary nucleic acid molecules that are complementary to the spacer segments of the probe and which themselves are labeled (for direct or indirect detection) are hybridized to said spacer segments to the probe.

Also provided by the invention are compositions of matter that include any of the nucleic acid hybridization probes hybridized to a target nucleic acid sequence of a target polynucleic acid molecule. The target nucleic acid molecule may, for example, be a naturally-occurring nucleic acid molecule or an otherwise biologically expressed nucleic acid molecule (such as the transcript of an artificial transgene). The target nucleic acid molecule may, for example, be a DNA molecule, such as a cellular genomic DNA, such as a chromosome, or viral DNA, or an RNA, such as cellular or viral RNA, such as a cellular or viral mRNA. The composition may, for example, include the probe hybridized to the target sequence in an in situ preparation of tissue or collected cells, such as but not limited to human cervical cells. The in situ preparation may include genomic DNA, for example, include or consist of one or more chromosomes, such as isolated human chromosomes, isolated non-human mammalian chromosomes, or isolated chromosomes of any desired organism and/or viral nucleic acids such as viral DNA or viral RNAs.

The spacer segment sequences may, for example, be uniform in length and/or sequence and/or at least some of the spacer segments may be different in length and/or sequence. The spacer segments may, for example, be from 10-200 monomers long or any subrange or numerical value in said range such as but not limited to 10-150, 10-100, 20-100, 10-50, 20-50, or 15-30 monomers long. The lengths of the segments of target-complementary sequence (the first nucleic acid segments) may, in at least some instances for a probe, for example, all instances, be in the range of 35-100 monomers long, or any subrange or numerical value therein, such as 50 monomers plus/minus 5 monomers long.

Figure 1A:
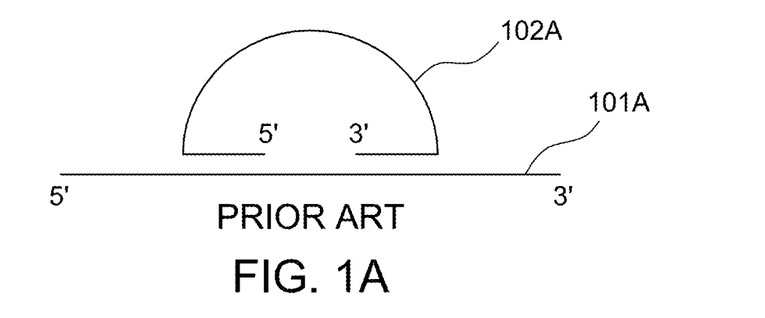
FIG. 1A schematically illustrates a prior art padlock-type probe hybridized to a target nucleic acid strand.

FIG. 1A schematically illustrates a prior art padlock-type probe (102A) hybridized to a target nucleic acid strand (101A). As shown, upon hybridization to a complementary target strand, this type of probe is contorted such that the 5' and 3' ends of the probe oppose each other in an adjacent manner (with the 5' and 3' end portions of the probe complementary to the target strand).

Figure 1B:
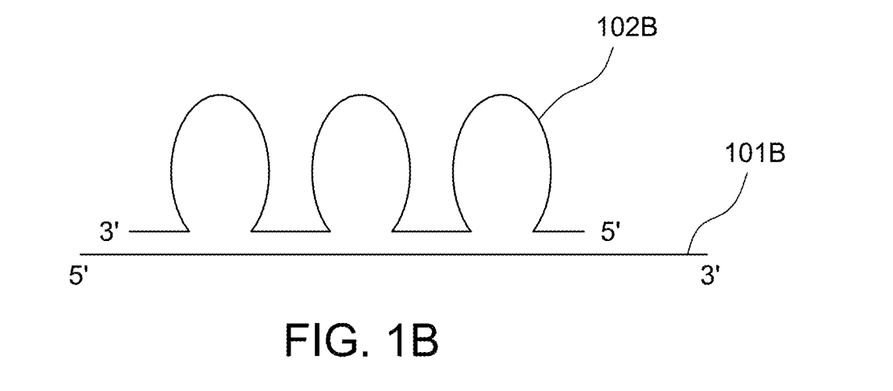
FIG. 1B schematically illustrates a nucleic acid hybridization probe embodiment of the invention having four segments complementary to a target nucleic acid strand and three intervening loop segments that are not complementary to the nucleic acid strand.

FIG. 1B schematically illustrates (not to scale) a nucleic acid hybridization probe embodiment of the invention (102B) having four segments complementary to a target nucleic acid strand (101B) and three intervening loop segments that are not substantially complementary to the nucleic acid strand.

Figure 1C:
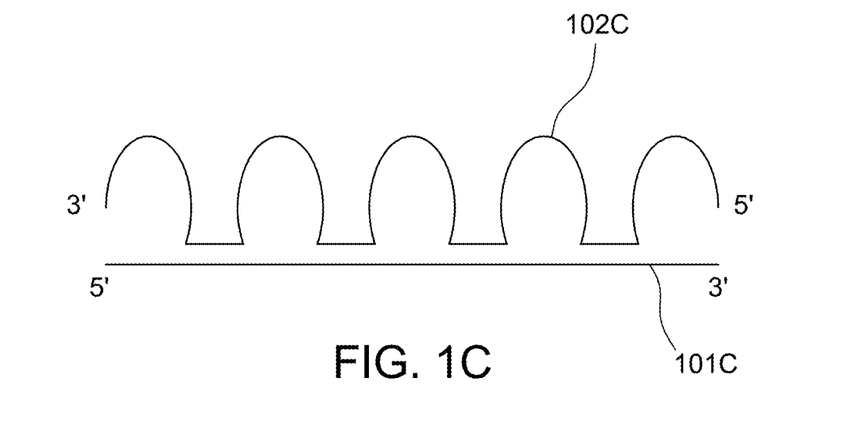
FIG. 1C schematically illustrates a nucleic acid hybridization probe embodiment of the invention similar to that shown in FIG. 1B but also including extra non-target-complementary sequence at the 5' and 3' termini of the probe.

FIG. 1C schematically illustrates (not to scale) a nucleic acid hybridization probe embodiment of the invention (102C) having four segments complementary to a target nucleic acid strand (101C), similar to that shown in FIG. 1B, but also including extra non-target-complementary sequence at the 5' and 3' termini of the probe.

Probes according to the invention specifically hybridize to a target nucleic acid molecule via the first segments of the probe that are complementary to sequences in the target nucleic acid molecule. The spacer segment sequences are selected so that they are at least substantially not complementary to the first segments or to the target nucleic acid molecule. In addition, the spacer segment sequence(s) may be selected so that they, and the overall probe, at least substantially do not hybridize to any non-target polynucleic acid molecules present in a specimen under the same conditions under which the probe specifically hybridizes via the first segments to a target nucleic acid molecule present in the specimen.

Example

The following example demonstrates the preparation of a biotin labeled RNA probe that is useful for in situ detection of HPV16 (human papilloma virus 16) transcripts in mammalian cells, such as isolated, fixed and permeabilized human cervical cells. Probes specifically binding selected transcripts of HPV16 were designed such that extra nucleic acid sequences, i.e., spacer segments with additional label, are interspersed in the target-complementary sequence. SEQ ID NO:1 (shown in Table 1) is the antisense (binding) strand DNA sequence of an HPV16 E6/E7 gene consensus sequence which served as the basis for preparing probes for detecting the E6 and E7 mRNAs of HPV16. It should be understood that the complementary DNA strand, i.e., the sense strand, is also present throughout preparation of the expression construct and will act as a template for synthesis of anti-sense RNA via transcription.

TABLE 1

(SEQ ID NO: 1)
gtagattatggtttctgagaacagatggggcacacaattcctagtgtgcccattaacaggtcttccaaagtacgaatgtctacgtgtgtgc tttgtacgcacaaccgaagcgtagagtcacacttgcaacaaaaggttacaatattgtaatgggctctgtccggttctgcttgtccagctg gaccatctatttcatcctcctcctctgagctgtcatttaattgctcataacagtagagatcagttgtctctggttgcaaatctaacatatattca tgcaatgtaggtgtatctccatgcatgattacagctgggtttctctacgtgttcttgatgatctgcaacaagacatacatcgaccggtccac cgacccettatattatggaatctttgcttttttgtccagatgtctttgcttttcttcaggacacagtggcttttgacagttaatacacctaattaac aaatcacacaacggtttgttgtattgctgttctaatgttgttccatacaaactataacaataatgtctatactcactaattttagaataaaactttt aaacatttatcacatacagcatatggattcccatctctatatactatgcataaatcccgaaaagcaaagtcatatacctcacgtcgcagta actgttgcttgcagtacacacattctaatattatatcatgtatagttgtttgcagctctgtgcataactgtggtaactttctgggtcgctcctgt gggtcctgaaacattgcagttctcttttggtgcataaaatgtctgcttttatactaaccggtttcggttcaaccgatttcggttacgcccttag ttttatacatgaattattgtagt The SEQ ID NO:1 DNA was modified by inserting the spacer sequence CACATTGCTCTCTTCCTTTC (SEQ ID NO:2) after every 50 bases, and at the beginning and end of the sequence, so that RNA transcribed from the template DNA strand will incorporate significant amounts of biotin-labeled cytosine and biotin-labeled uracil ribonucleotide residues in transcribing the spacer segments in addition to those incorporated in transcribing the target (E6/E7 RNA)-complementary sequences. The resulting modified DNA sequence (SEQ ID NO:3) is shown in Table 2 with the inserted spacer sequences indicated in capital letters. The spacer sequence is internally inserted seventeen times and occurs once at each end.

TABLE 2

(SEQ ID NO: 3)
```
CACATTGCTCTCTTCCTTTCgtagattatggtttctgagaacagatggggcacacaattcctagtgtgccCACATT GCTCTCTTCCTTTCcattaacaggtcttccaaagtacgaatgtctacgtgtgtgctttgtacgcCACATTGCTCTCT TCCTTTCacaaccgaagcgtagagtcacacttgcaacaaaaggttacaatattgtaaCACATTGCTCTCTTCCTT TCtgggctctgtccggttctgcttgtccagctggaccatctatttcatcctcCACATTGCTCTCTTCCTTTCctcctctga gctgtcatttaattgctcataacagtagagatcagttgtctCACATTGCTCTCTTCCTTTCctggttgcaaatctaacatat attcatgcaatgtaggtgtatctccatgcCACATTGCTCTCTTCCTTTCatgattacagctgggtttctctacgtgttcttga tgatctgcaacaagacCACATTGCTCTCTTCCTTTCatacatcgaccggtccaccgacccct tatattatggaatctttg cttttt CACATTGCTCTCTTCCTTTCgtccagatgtctttgcttttcttcaggacacagtggcttttgacagttaaCACA TTGCTCTCTTCCTTTCtacacctaattaacaaatcacacaacggtttgttgtattgctgttctaatCACATTGCTCTC TTCCTTTCgttgttccatacaaactataacaataatgtctatactcactaattttagaCACATTGCTCTCTTCCTTTC ataaaactttaaacatttatcacatacagcatatggattcccatctctatCACATTGCTCTCTTCCTTTCatactatgcataa atcccgaaaagcaaagtcatatacctcacgtcgcagtCACATTGCTCTCTTCCTTTCaactgttgcttgcagtacacac attctaatattatatcatgtatagttgtCACATTGCTCTCTTCCTTTCttgcagctctgtgcataactgtggtaactttctggg tcgctcctgtgggtCACATTGCTCTCTTCCTTTCcctgaaacattgcagttctcttttggtgcataaaatgtctgcttttata cCACATTGCTCTCTTCCTTTCtaaccggtttcggttcaaccgatttcggttacgcccttagttttatacatCACATTG CTCTCTTCCTTTCgaattattgtagtCACATTGCTCTCTTCCTTTC
```

The SEQ ID NO:3 modified template DNA was placed after a T7 promoter in a plasmid expression vector for in vitro transcription using T7 RNA polymerase and RNA was transcribed in vitro from the isolated plasmid using the Enzo BIOARRAY HIGHYIELD® RNA transcript labeling kit (T7) (Product No. ENZ-42655; Enzo Life Sciences, Inc., Farmingdale, N.Y., USA). The transcribed RNA, which includes biotin-labeled cytosine and biotin-labeled uracil ribonucleotide residues, was then hydrolyzed by alkaline hydrolysis to an average size of 200 bases using sodium carbonate/bicarbonate buffer. The resulting biotin labeled RNA fragments were used as a hybridization probe composition to detect nucleic acids in cells in situ using conventional techniques. Similar probes were also made for the HPV16 L1 gene, L2 gene, and E1 gene. E2 gene probes as well as probes for other genes and RNAs may also be made.

In the above example, optional terminal occurrences of the spacer sequence were added. It should be understood that, generally, in addition to internal spacer sequence insertions, a spacer sequence may be added at both termini, at one end only (at the 5' end or the 3' end with respect to the antisense sequence), or not at either termini.

Figure 2A:
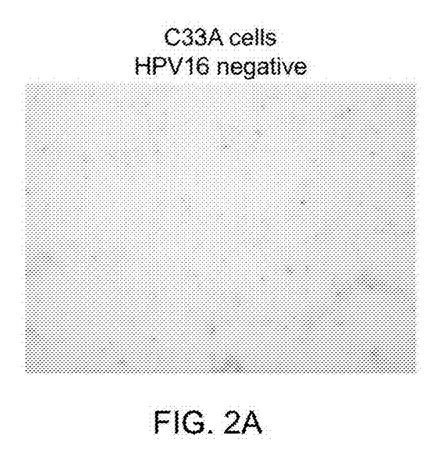
FIG. 2A is a photomicrograph showing the in situ hybridization results of an HPV E6/E7 RNA hybridization probe embodiment of the invention to C33A negative control cells, which lack an integrated HPV genome.

FIG. 2A is a photomicrograph showing the in situ hybridization results of the HPV E6/E7 RNA hybridization probe embodiment of the example (having SEQ ID NO:3) to C33A negative control cells, which lack an integrated HPV genome.

Figure 2B:
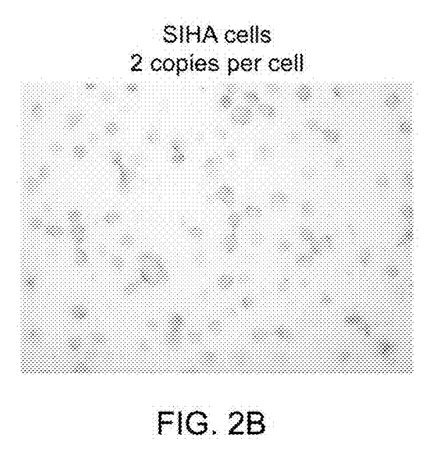
FIG. 2B is a photomicrograph showing the in situ hybridization results of the same HPV E6/E7 RNA hybridization probe embodiment as used for FIG. 2A but to SIHA cells, which have two integrated HPV-16 genomes per cell.

FIG. 2B is a photomicrograph showing the in situ hybridization results of the same HPV E6/E7 RNA hybridization probe of the example but to SIHA cells, which have two integrated HPV-16 genomes per cell.

Figure 2C:
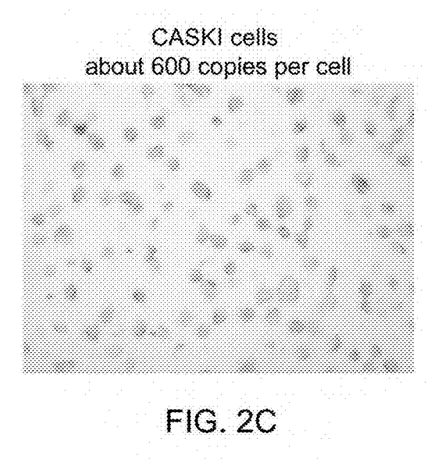
FIG. 2C is a photomicrograph showing the in situ hybridization results of the same HPV E6/E7 RNA hybridization probe embodiment as used for FIG. 2A but to CASKI cells, which have about 600 integrated HPV-16 genomes per cell.

FIG. 2C is a photomicrograph showing the in situ hybridization results of the same HPV E6/E7 RNA hybridization probe of the example but to CASKI cells, which have about 600 integrated HPV-16 genomes per cell.

In a separate experiment, a mixture of fragmented loop RNA hybridization probes according to the invention that cover substantially all of the HPV-16 genome was prepared and tested. Photomicrographs showing the results with this HPV genome-spanning mixture of probes are shown in FIGS. 3A-3C as follows.

Figure 3A:
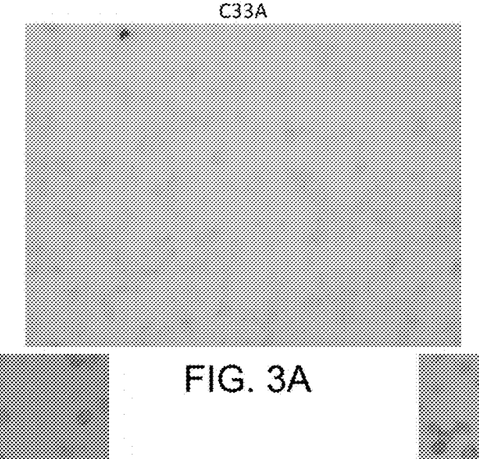
FIG. 3A is a photomicrograph showing the in situ hybridization results of a HPV genome spanning mixture of RNA hybridization probes according to an embodiment of the invention to C33A negative control cells.

FIG. 3A is a photomicrograph showing the in situ hybridization results of the HPV genome-spanning mixture of RNA hybridization probes to C33A negative control cells.

Figure 3B:
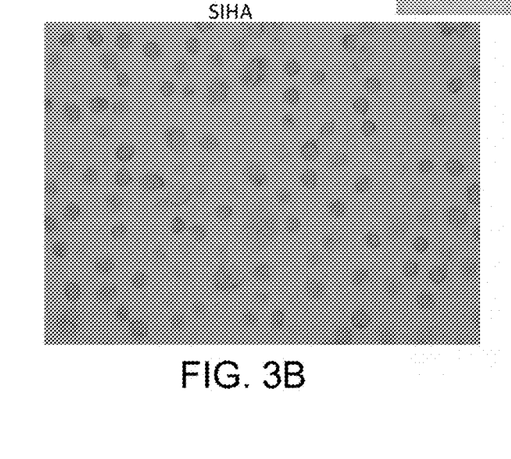
FIG. 3B is a photomicrograph showing the in situ hybridization results of the same RNA probe mixture as used for FIG. 3A but to SIHA cells, which have two integrated HPV-16 genomes per cell.

FIG. 3B is a photomicrograph showing the in situ hybridization results of the same RNA probe mixture to SIHA cells, which have two integrated HPV-16 genomes per cell.

Figure 3C:
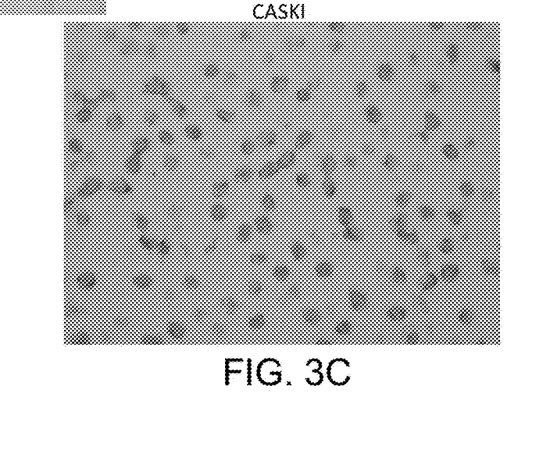
FIG. 3C is a photomicrograph showing the in situ hybridization results of the same RNA probe mixture as used for FIG. 3A but to CASKI cells, which have about 600 integrated HPV-16 genomes per cell.

FIG. 3C is a photomicrograph showing the in situ hybridization results of the same RNA probe mixture to CASKI cells, which have about 600 integrated HPV-16 genomes per cell.

As described, long enzymatically synthesized RNA transcripts may be partially alkaline hydrolyzed to provide a mixture of smaller fragments useful as probes. The mixture may, for example, include fragments in the range of 100-500 residues long, such as 200-400 residues long, such as 250-350 residues long, or any subranges therein. The mixture may, for example, include a substantial fraction of fragments in these size ranges. The mixture of size fragments obtained by the partial alkaline hydrolysis may, if desired, be further size fractionated or enriched, for example, by column chromatography, to obtain a mixture of fragments having a substantial fraction of fragments in the desired size ranges, such as but not limited to the aforementioned size ranges and subranges.

The following protocol may be used to partially alkaline hydrolyze labeled transcribed RNA, such as the biotin-labeled RNA transcripts of the example. 100 μl transcribed RNA (20 μg total) is mixed with 100 μl Hydrolysis Buffer (80 mM NaHCO$_3$, 120 mM Na2CO3, 20 mM β-mercaptoethanol) and heated to 60° C. for 25 minutes. 200 μl Stop Buffer (200 mM sodium acetate, pH 6, 1% Acetic acid, 10 mM dithiothreitol) is then added, after which 40.88 μl 3 M sodium acetate, pH 5.2 and 8.77 μl Yeast tRNA (11.4 mg/ml)

are added. Finally, 1124 µl ethanol is added with mixing, and the mixture is stored at −80° C. for 2 hours. The fragmented RNA is then precipitated by centrifugation at 4° C. at 16,000×g for 20 minutes at 4° C. The supernatant is carefully removed, and the pellet is washed with 700 µl ice cold 70% ethanol, and centrifuged again at 16,000×g for 5 minutes at 4° C. The supernatant is again removed, and the tube spun a second time for 15 seconds to bring all the remaining liquid down, which is then removed. The pelleted fragmented RNA is then resuspended in 100 µl of 10 mM TrisHCl, pH 7.0, 1 mM EDTA to form an RNA Hybridization Probe Stock Solution.

Single-stranded DNA probes may also be synthesized enzymatically. For example, a pair of peripheral DNA PCR primers may be used to amplify by PCR a double-stranded DNA molecule, which is SEQ ID NO: 3 hybridized to its complement, in a reaction including digoxigenin-labeled cytosine deoxynucleotides (dCTP) and digoxigenin-labeled uracil deoxynucleotides (dUTP), and/or, for example, fluorescently labeled versions of these same deoxynucleotides. One of the PCR primers of the pair, such as the one that extends the sense strand of the amplicon, may be labeled with biotin so that the sense strand can be bound to an avidin or streptavidin support/bead and separated from the antisense strand, e.g., using NaOH, while biotin-streptavidin binding remains unperturbed. The isolated, labeled, antisense DNA strand can then be used as a single-stranded hybridization probe, for example, for detecting particular mRNAs. The isolated, single-stranded, anti-sense DNA may be used directly as a probe and/or may be fragmented, for example, into a probe composition of fragments, for example, having average length of 180-220 bases. Fragmentation of single-stranded DNA may be performed by any suitable method such as Point-sink Shearing (PtS; Thorstenson et al., *An Automated Hydrodynamic Process for Controlled, Unbiased DNA Shearing*, Genome Res. 1998 August; 8(8): 848-855); acoustical shearing such as Covaris truSHEAR™ Mechanical DNA Shearing (Covaris, Inc., Woburn, Mass., USA), needle shearing (by creating shearing forces by passing DNA through a small gauge needle), nebulization-based (using compressed air to force DNA through a small hole in a nebulizer unit, and collecting the fragmented, aerosolized DNA-DNA fragment size is determined by the pressure used), and DNAse I treatment.

Still other enzymatic methods for producing single-stranded DNA hybridization probes according to the invention include asymmetric PCR (using labeled nucleotides) and rolling circle amplification (using labeled nucleotides). See Marimuthu et al., *Single-stranded DNA (ssDNA) production in DNA aptamer generation*, Analyst, 2012, 137, 1307 for a review of methods for producing single-stranded DNA that are readily adaptable to production of single-stranded DNA probes according to the invention. The labeled single-stranded DNA molecules according to the invention that may be obtained using these or any methods may, optionally, also be fragmented to obtain probe compositions as described above.

Various fluorescently labeled and hapten-labeled ribonucleotides and deoxynucleotides are commercially available for polymerase-mediated synthesis of probes according to the invention, such as but not limited to Cyanine 3 UTP enhanced (ENZ-42505; Enzo Life Sciences), Cyanine 5-UTP enhanced (ENZ-42506), Fluorescein-12-UTP (ENZ-42834), Biotin-11-CTP (ENZ-42818), Biotin-16-UTP (ENZ-42814), Digoxigenin-UTP alkali-stable (ENZ-NUC114-0250), Cyanine 3-dUTP (ENZ-42501), Cyanine 5 dUTP (ENZ-42502), and Digoxigenin-dUTP alkali-stable (ENZ-NUC113-0025). Rather than directly enzymatically incorporating fluorescently labeled or hapten-labeled nucleotides into the probes, allyl amine labeled nucleotides (aminoallyl nucleotides), such as but not limited to aminoallyl dUTP (ENZ-42861) and aminoallyl UTP (R1091, ThermoFisher Scientific), may be incorporated and then reacted with fluorescent dye or hapten derivatives to functionally label the probe, as known in the art. The aminoallyl nucleotides are reactive with N-hydroxysuccinimide (NETS) ester groups of commercially available label derivatives to form a bond with the primary amino group of the nucleotide. As to chemical synthesis of nucleic acid probes according to the invention, a variety of labeled phosphoramidites are available for incorporation into an oligonucleotide, such as into the loop portions of probes according to the invention, by phosphoramidite chemistry such as but not limited to biotin phosphoramidite (e.g., M042000, Millipore Sigma), Cyanine 3 phosphoramidite (e.g., M047000, Millipore Sigma), Cyanine 5 phosphoramidite (e.g., M046030, Millipore Sigma), fluorescein phosphoramidite (e.g., M041080, Millipore Sigma), 6-fluorescein phosphoramidite (e.g., M041100, Millipore Sigma) and 6-hexachloro-fluorescein phosphoramidite (e.g., M043130, Millipore Sigma).

The invention also provides nucleic acid "spacer segmented" probes labeled as described along with the aforementioned variations thereof, as well as corresponding probe embodiments that are not labeled but which otherwise have the same structure (and optionally any or all of the variations thereof described herein), for hybridization to a target nucleic acid molecule, such as a naturally occurring target nucleic acid molecule, and detection by labeled nucleic acid probes, such as labeled oligonucleotide probes, that are complementary to and hybridize with one or more or all of the spacer segments of the nucleic acid "spacer segmented" probes.

Accordingly, one embodiment of the invention provides a non-naturally occurring linear nucleic acid molecule having a 5' end and a 3' end, which includes:

a series of first nucleic acid segments consecutively complementary to a preselected nucleic acid target sequence; and between each adjacent pair of first nucleic acid segments, a spacer nucleic acid segment, wherein the spacer segments are not substantially complementary to the preselected nucleic acid target sequence.

At least some nucleic acid monomers (residues) of the spacer segments may be labeled with detectable labels or none of the nucleic acid monomers of the spacer segments may be labeled with detectable labels, such as none of the nucleic acid monomers of the non-naturally occurring linear nucleic acid molecule are labeled with detectable labels.

A further embodiment of the invention provides a composition of matter that includes this non-naturally occurring linear nucleic acid molecule and one or more labeled nucleic acid probes, such as labeled oligonucleotide probes, that are complementary to and hybridized with one or more or all of the spacer segments of said non-naturally occurring linear nucleic acid molecule.

Another embodiment of the invention provides a composition of matter that includes this non-naturally occurring linear nucleic acid molecule and a naturally occurring target nucleic acid molecule to which the non-naturally occurring linear nucleic acid molecule is hybridized by way of the first nucleic acid segments.

A still further embodiment of the invention provides a composition of matter that includes:

the aforementioned non-naturally occurring linear nucleic acid molecule (either labeled or unlabeled);

one or more labeled nucleic acid hybridization probes, such as labeled oligonucleotide probes, that are complementary to and hybridized with one or more or all of the spacer segments of said non-naturally occurring linear nucleic acid molecule; and a naturally occurring target nucleic acid molecule to which the non-naturally occurring linear nucleic acid molecule is hybridized by way of the first nucleic acid segments.

For embodiments including a labeled non-naturally occurring linear nucleic acid as described and one or more labeled nucleic acid probes hybridized to the spacer segments thereof, the detectable labels of the former and the latter may be entirely the same type, entirely different types, or have at least one detectable label type in common and also have at least one detectable label type not in common.

Unlabeled non-naturally occurring linear nucleic acid molecule embodiments of the invention (and fragmented probe composition embodiments derived therefrom) may be prepared using the same method embodiments disclosed herein for labeled embodiments by leaving out the labeled nucleic acid monomers, i.e., by using only unlabeled nucleic acid monomers. Such unlabeled non-naturally occurring linear nucleic acid molecule embodiments of the invention may also be fragmented as described herein to provide a fragmented probe composition (optionally with any or all of the same variations and further processing of fragmented compositions described herein with respect to labeled embodiments).

A still further embodiment of the invention provides a method for detecting a target nucleic acid sequence in a sample that includes the steps of:

providing a non-naturally occurring nucleic acid molecule (labeled or unlabeled and fragmented or unfragmented) as described herein;

providing detectably labeled nucleic acid hybridization probes, such as but not limited to oligonucleotide probes, that are complementary to and capable of hybridization with spacer segments of the non-naturally occurring nucleic acid molecule;

contacting the non-naturally occurring nucleic acid molecule with an isolated biological sample that may contain nucleic acid molecules that include the preselected nucleic acid target sequence under conditions permitting hybridization of the non-naturally occurring nucleic acid molecule to the nucleic acid molecules including the preselected nucleic acid target sequence if present in the sample;

washing away unhybridized non-naturally occurring nucleic acid molecule from the isolated biological sample;

contacting the detectably labeled nucleic acid probes with the isolated biological sample so that said probes hybridize with spacer segments of any of the non-naturally occurring nucleic acid molecule that hybridized to the target nucleic acid molecule if present;

washing away unhybridized detectably labeled nucleic acid hybridization probes from the isolated biological sample; and detecting label of any of the detectably labeled nucleic acid hybridization probes that remains in the isolated biological sample.

In one variation, the isolated biological sample contains the target nucleic molecule and it is detected by the method. The detecting step may include a 2D or 3D visualization/image capture using microscopy as known in the art. If the non-naturally occurring nucleic acid molecule also includes detectable labels, they may also be detected. For example, if the detectable labels of the non-naturally occurring nucleic acid molecule are the same as those of the nucleic acid probes, all of the detectable labels may be detected in the same detecting step. However, if the detectable labels of the non-naturally occurring nucleic acid molecule and those of the nucleic acid probes are orthogonally detectable, the method may include a further step of detecting label of the non-naturally occurring nucleic acid molecule that remains in the biological sample (after the first washing step and/or after the second washing step). The invention also provides a corresponding embodiment in which the non-naturally occurring nucleic acid molecule and the nucleic acid probes are first contacted with the isolated biological sample under conditions permitting nucleic acid hybridization at the same time, and may, for example, be mixed together before or during said contact with the isolated biological sample, followed by washing and detection of label remaining in the sample.

Any and all publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s). Moreover, features described in connection with one embodiment of the invention may be used in conjunction with other embodiments, even if not explicitly exemplified in combination within.

What is claimed is:

1. A method for preparing a nucleic acid hybridization probe composition for a nucleic acid target of interest, comprising the steps of:
providing an in vitro mixture of
(a) a DNA construct comprising an RNA promoter operably linked to a template DNA sequence, wherein the template sequence encodes a non-naturally occurring linear nucleic acid molecule having a 5' end and a 3' end and comprising
a series of first nucleic acid segments consecutively complementary to a preselected nucleic acid target sequence, and
between each adjacent pair of first nucleic acid segments, a spacer nucleic acid segment,
wherein the spacer segments are not substantially complementary to the preselected nucleic acid target sequence, and
wherein the spacer segments are not substantially complementary to the first segments,
(b) a mixture of different ribonucleoside triphosphates wherein at least some of said ribonucleoside triphosphates are chemically labeled;
(c) an RNA polymerase capable of transcribing an RNA molecule comprising residues of the chemically labeled ribonucleoside triphosphates from the template under control of the promoter;
incubating said mixture under conditions permissive for transcription of the RNA molecule by the RNA polymerase, wherein said RNA molecule is thereby transcribed in quantity; and
partially fragmenting the quantity of RNA molecule obtained by transcription in the incubating step to obtain a fragmented nucleic acid hybridization probe composition.

2. The method of claim 1, wherein the chemically labeled ribonucleoside triphosphates comprise a hapten label.

3. The method of claim 2, wherein the hapten label is selected from the group consisting of biotin and digoxigenin.

4. The method of claim 1, wherein the chemically labeled ribonucleoside triphosphates comprise a fluorescent label.

5. The method of claim 1, wherein the chemically labeled ribonucleoside triphosphates comprise an allyl amine group label.

6. A method for preparing a nucleic acid hybridization probe composition for a nucleic acid target of interest, comprising the steps of:
providing an in vitro mixture of
(a) a nucleic acid template molecule, wherein the template sequence encodes a non-naturally occurring linear nucleic acid molecule having a 5' end and a 3' end and including
a series of first nucleic acid segments consecutively complementary to a preselected nucleic acid target sequence, and
between each adjacent pair of first nucleic acid segments, a spacer nucleic acid segment,
wherein the spacer segments are not substantially complementary to the preselected nucleic acid target sequence;
(b) a template-directed nucleic acid polymerase capable of synthesizing a nucleic acid molecule comprising residues of chemically labeled nucleoside triphosphates and complementary to at least part of the template using the template molecule, and
(c) a mixture of different nucleoside triphosphates wherein at least some of said nucleoside triphosphates are chemically labeled;
incubating said mixture under conditions permissive for template-directed nucleic acid synthesis by the polymerase, wherein said nucleic acid molecule including residues of the chemically labeled nucleoside triphosphates and complementary to at least part of the template is thereby synthesized in quantity by the polymerase using the template; and
partially fragmenting the quantity of the synthesized nucleic acid molecule comprising residues of chemically labeled nucleoside triphosphates and complementary to at least part of the template to obtain a fragmented nucleic acid hybridization probe composition.

7. The method of claim 6, wherein the chemically labeled ribonucleoside triphosphates comprise a hapten label.

8. The method of claim 7, wherein the hapten label is selected from the group consisting of biotin and digoxigenin.

9. The method of claim 6, wherein the chemically labeled ribonucleoside triphosphates comprise a fluorescent label.

10. The method of claim 6, wherein the chemically labeled ribonucleoside triphosphates comprise an allyl amine group label.

* * * * *

SEQUENCE LISTING

```
<160> NUMBER OF SEQ ID NOS: 3

<210> SEQ ID NO 1
<211> LENGTH: 863
<212> TYPE: DNA
<213> ORGANISM: Human papillomavirus type 16

<400> SEQUENCE: 1
gtagattatg gtttctgaga acagatgggg cacacaattc ctagtgtgcc cattaacagg      60
tcttccaaag tacgaatgtc tacgtgtgtg ctttgtacgc acaaccgaag cgtagagtca     120
cacttgcaac aaaaggttac aatattgtaa tgggctctgt ccggttctgc ttgtccagct     180
ggaccatcta tttcatcctc ctcctctgag ctgtcattta attgctcata acagtagaga     240
```

```
tcagttgtct ctggttgcaa atctaacata tattcatgca atgtaggtgt atctccatgc    300
atgattacag ctgggtttct ctacgtgttc ttgatgatct gcaacaagac atacatcgac    360
cggtccaccg accccttata ttatggaatc tttgcttttt gtccagatgt ctttgctttt    420
cttcaggaca cagtggcttt tgacagttaa tacacctaat taacaaatca cacaacggtt    480
tgttgtattg ctgttctaat gttgttccat acaaactata acaataatgt ctatactcac    540
taattttaga ataaaacttt aaacatttat cacatacagc atatggattc ccatctctat    600
atactatgca taaatcccga aaagcaaagt catataccte acgtcgcagt aactgttgct    660
tgcagtacac acattctaat attatatcat gtatagttgt ttgcagctct gtgcataact    720
gtggtaactt tctgggtcgc tcctgtgggt cctgaaacat tgcagttctc ttttggtgca    780
taaaatgtct gcttttatac taaccggttt cggttcaacc gatttcggtt acgcccttag    840
ttttatacat gaattattgt agt                                            863

<210> SEQ ID NO 2
<211> LENGTH: 20
<212> TYPE: DNA
<213> ORGANISM: Artificial Sequence
<220> FEATURE:
<223> OTHER INFORMATION: Spacer sequence that introduces labeling
      positions

<400> SEQUENCE: 2
cacattgctc tcttcctttc                                                 20

<210> SEQ ID NO 3
<211> LENGTH: 1243
<212> TYPE: DNA
<213> ORGANISM: Artificial Sequence
<220> FEATURE:
<223> OTHER INFORMATION: HPV E6-E7 consensus sequence with spacer
      sequences inserted every 50 bases and at termini

<400> SEQUENCE: 3
cacattgctc tcttcctttc gtagattatg gtttctgaga acagatgggg cacacaattc     60
ctagtgtgcc cacattgctc tcttcctttc cattaacagg tcttccaaag tacgaatgtc    120
tacgtgtgtg ctttgtacgc cacattgctc tcttcctttc acaaccgaag cgtagagtca    180
cacttgcaac aaaaggttac aatattgtaa cacattgctc tcttcctttc tgggctctgt    240
ccggttctgc ttgtccagct ggaccatcta tttcatcctc cacattgctc tcttcctttc    300
ctcctctgag ctgtcattta attgctcata acagtagaga tcagttgtct cacattgctc    360
tcttcctttc ctggttgcaa atctaacata tattcatgca atgtaggtgt atctccatgc    420
cacattgctc tcttcctttc atgattacag ctgggtttct ctacgtgttc ttgatgatct    480
gcaacaagac cacattgctc tcttcctttc atacatcgac cggtccaccg accccttata    540
ttatggaatc tttgcttttt cacattgctc tcttcctttc gtccagatgt ctttgctttt    600
cttcaggaca cagtggcttt tgacagttaa cacattgctc tcttcctttc tacacctaat    660
taacaaatca cacaacggtt tgttgtattg ctgttctaat cacattgctc tcttcctttc    720
gttgttccat acaaactata acaataatgt ctatactcac taattttaga cacattgctc    780
tcttcctttc ataaaacttt aaacatttat cacatacagc atatggattc ccatctctat    840
cacattgctc tcttcctttc atactatgca taaatcccga aaagcaaagt catatacctc    900
acgtcgcagt cacattgctc tcttcctttc aactgttgct tgcagtacac acattctaat    960
```

```
attatatcat gtatagttgt cacattgctc tcttcctttc ttgcagctct gtgcataact    1020
gtggtaactt tctgggtcgc tcctgtgggt cacattgctc tcttcctttc cctgaaacat    1080
tgcagttctc ttttggtgca taaaatgtct gcttttatac cacattgctc tcttcctttc    1140
taaccggttt cggttcaacc gatttcggtt acgcccttag ttttatacat cacattgctc    1200
tcttcctttc gaattattgt agtcacattg ctctcttcct ttc                      1243
```